US006897027B2

(12) United States Patent
Smárason et al.

(10) Patent No.: US 6,897,027 B2
(45) Date of Patent: May 24, 2005

(54) METHOD FOR DESALTING NUCLEIC ACIDS

(75) Inventors: Sigurdur V. Smárason, Reykjavik (IS); Albert V. Smith, Reykjavik (IS)

(73) Assignee: deCODE genetics ehf., Reykjavik (IS)

( * ) Notice: Subject to any disclaimer, the term of this patent is extended or adjusted under 35 U.S.C. 154(b) by 260 days.

(21) Appl. No.: 10/109,587

(22) Filed: Mar. 27, 2002

(65) Prior Publication Data

US 2003/0186247 A1 Oct. 2, 2003

(51) Int. Cl.$^7$ ........................... C12Q 1/68; C12P 19/34; C07H 21/02; C07H 21/04
(52) U.S. Cl. ....................... 435/6; 435/91.2; 536/23.1; 536/24.31; 536/24.33
(58) Field of Search ................. 435/6, 91.2; 536/23.1, 536/24.1; 210/87, 488, 638; 423/308

(56) References Cited

U.S. PATENT DOCUMENTS

| | | | |
|---|---|---|---|
| 3,485,763 A | 12/1969 | Lefevre et al. | 252/179 |
| 4,025,608 A | 5/1977 | Tawil et al. | 423/305 |
| 4,059,679 A | 11/1977 | Clearfield | 423/306 |
| 4,152,176 A | 5/1979 | Guhde | 148/6.15 R |
| 4,381,289 A | 4/1983 | Nowell et al. | 423/311 |
| 4,521,528 A | 6/1985 | Kovach | 502/208 |
| 4,629,656 A | 12/1986 | Alberti et al. | 428/411.1 |
| 4,826,663 A | 5/1989 | Alberti et al. | 423/157 |
| 5,141,634 A | 8/1992 | Carr et al. | 210/198.2 |
| 5,514,490 A | 5/1996 | Chen et al. | 429/191 |
| 6,136,555 A | 10/2000 | Jones | 435/41 |
| 6,241,980 B1 | 6/2001 | Collis et al. | 424/78.11 |
| 2003/0152974 A1 * | 8/2003 | Gauch et al. | 435/6 |

OTHER PUBLICATIONS

Inoue et al.(Journal of chromatography, 645 (1993) 57–65).*
Augustyniak et al.(Analytical Biochemistry 69, 310–311 (1975)).*
Alberti et al.(Journal of Inorganic Nucl. Chem., vol. 30, pp. 317–318 (1968)).*
Gilar et al.(Journal of Chromatography A, 921 (2001) pp. 3–13).*
Marashi et al(Biotechniques, May/Jun. 1985).*
Zon et al(Biochromatography, vol. 1., No. 1 (1986)).*
Oxtoby, D. W., et al., *Chemistry: Science of Change*, Orlando, Florida, Holt, Rinehart & Winston, Inc., 1990, p. 346–347.
Griffin, T. J., et al. "Single–Nucleotide Polymorphism Analysis by MALDI–TOF Mass Spectrometry," *Trends Biotechnol.*, 18(2), 77–84 (2000).
Fu, D.–J., et al. "Sequencing Exons 5 to 8 of the *p53* Gene by MALDI–TOF Mass Spectrometry," *Nature Biotechnol.*, 16:381–384 (1998).
Schafer, A. J., et al. "DNA Variation and the Future of Human Genetics," *Nature Biotechnol.*, 16:33–39 (1998).
Wang, D. G., et al. "Large–Scale Identification, Mapping, and Genotyping of Single–Nucleotide Polymorphisms in the Human Genome" *Science*, 280:1077–1082 (1998).

Kowalski, P., et al. "Accelerating Discoveries in the Proteome and Genome with MALDI TOF MS" *Pharmacogenomics*, 1(3) :359–366 (2000).
Van de Water, J., et al. "Detection of Molecular Determinants in Complex Biological Systems Using MALDI–TOF Affinity Mass Spectrometry", *Methods Mol. Biol.*, 146:453–459 (2000).
Purcell, A. W., et al., "The Use of Post–Source Decay in Matrix–Assisted Laser Desorption/Ionisation Mass Spectrometry to Delineate T Cell Determinants", *J. Immunol. Methods*, 249(1–2) :17–31 (2001).
Collins, F. S., et al. "New Goals for the U.S. Human Genome Project: 1998–2003," *Science*, 282:682–689 (1998).
Jurinke, C., et al., "Analysis of Ligase Chain Reaction Products via Matrix–Assisted Laser Desorption/Ionization Time–of–Flight–Mass Spectrometry," *Anal. Biochem.*, 237(2) :174–181 (1996).
Braun, A., et al., "Improved Analysis of Microsatellites Using Mass Spectrometry," *Genomics*, 46:18–23 (1997).
Köster, H., et al., "A Strategy for Rapid and Efficient DNA Sequencing by Mass Spectrometry," *Nature Biotechnol.*, 14:1123–1128 (1996).
Little, D. P., et al., "Mass Spectrometry from Miniaturized Arrays for Full Comparative DNA Analysis," *Nature Med.*, 3(12) :1413–1416 (1997).
Hurst, G. B., et al., "Detection of Bacterial DNA Polymerase Chain Reaction Products by Matrix–Assisted Laser Desorption/Ionization Mass Spectrometry," *Rapid Commun. Mass Spectrom.*, 10:377–382 (1996).
Clearfield, A., et al., "The Preparation of Crystalline Zirconium Phosphate and Some Observations on Its Ion Exchange Behaviour," *J. Inorg. Nucl. Chem.*, 26:117–129 (1964).
Alberti, G., et al., "Crystalline Insoluble Salts of Polybasic Metals—II. Synthesis of Crystalline Zirconium or Titanium Phosphate by Direct Precipitation," *J. Inorg. Nucl. Chem.*, 30:317–318 (1968).
Little, D. P., et al., "Identification of Apolipoprotein E Polymorphisms Using Temperature Cycled Primer Oligo Base Extension and Mass Spectrometry," *Eur. J. Clin. Chem. Clin. Biochem.*, 35(7) :545–548 (1997).

(Continued)

*Primary Examiner*—Jeffrey Fredman
*Assistant Examiner*—Sally A. Sakelaris
(74) *Attorney, Agent, or Firm*—Hamilton, Brook, Smith & Reynolds, P.C.

(57) ABSTRACT

The present invention relates to a method for desalting nucleic acid samples. The method involves contacting a liquid sample comprising a nucleic acid and an ionic salt with an ion exchanger comprising an insoluble phosphate salt, removing said liquid, and eluting said nucleic acid from the ion exchanger. The desalted nucleic acids provided by the methods of the invention are suitable for a wide variety of analytic and diagnostic applications, including high-throughput assays.

33 Claims, 2 Drawing Sheets

OTHER PUBLICATIONS

Jurinke, C., et al., "Detection of Hepatitis B Virus DNA in Serum Samples Via Nested PCR and MALDI–TOF Mass Spectrometry," *Genetic Analysis: Biomolecular Engineering,* 13:67–71 (1996).

Higgins, G. S., et al., "Competitive Oligonucleotide Single–Base Extension Combined with Mass Spectrometric Detection for Mutation Screening," *Biotechniques,* 23(*4*): 710–714 (1997).

* cited by examiner

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1
taatacgact cactataggg aga                                           23

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
attaaccctc actaaaggga                                               20

METHOD FOR DESALTING NUCLEIC ACIDS

BACKGROUND OF THE INVENTION

In recent years, the need for high throughput strategies for the analysis of biological samples has increased dramatically. One area of development is the design of high throughput techniques for the analysis of nucleic acids. Analysis of nucleic acids frequently requires that they be separated from various impurities generated during synthesis or isolation.

A common impurity in a sample of nucleic acids is salt. Many analytic and diagnostic assays of nucleic acids require that salts be removed from nucleic acid samples prior to analysis. Often times, this necessitates one or more separation and/or purification steps in order to desalt the sample comprising the nucleic acid.

One analytic technique which often requires desalting of nucleic acid samples is matrix-assisted laser desorption-ionization-time-of-flight (MALDI-TOF) mass spectrometry (MS) (MALDI-TOF MS) (see, e.g., Griffin, T. J. and Smith, L. M., *Trends Biotechnol.* 18:77–84 (2000)). When used to analyze nucleic acids, MALDI-TOF MS involves laser-induced desorption and ionization of nucleic acid molecules which are embedded in a large excess of a crystalline matrix. Laser-induced desorption and ionization of nucleic acid molecules results in production of ions that acquire the same initial energy when accelerated in an electric field, and allows for separation of nucleic acids based on mass-to-charge ratios when performed in high vacuum.

Desalting of nucleic acid samples is necessary for MALDI-TOF, MS analysis of nucleic acids because the positive ions (cations) of a salt can interact with the negatively-charged sugar phosphate backbone of the nucleic acid, resulting in signal dilution and complicating data analysis.

Several methods for desalting nucleic acid samples are currently available, including dialysis, solid phase extraction techniques, size exclusion filtration techniques, affinity capture techniques including magnetic bead binding and washing, ethanol precipitation and ion exchange. With the exception of ion exchange, these desalting methods all require one or more washing and/or separation steps in order to remove the salt from the nucleic acid. Moreover, all of these desalting methods, with the exception of ion exchange, suffer from complications when subjected to high-throughput analysis. For example, magnetic bead desalting can be difficult to automate, solid phase extraction techniques can suffer from cross talk when used in a 96- or 384-well format, and size exclusion filtration techniques can result in the loss of sample during filtration and/or resuspension steps. Further, these techniques require movement of sample plates to and from filter stations and/or specialized equipment, which can be difficult and costly to fully automate.

While ion exchange can eliminate washing and/or separation steps and is suitable for high-throughput analysis, there are other problems associated with the use of ion exchange to desalt nucleic acids. For example, gel-based ion exchangers have typically been used to desalt nucleic acids. However, gel-based ion exchangers can absorb liquid, as well as ions. For dilute solutions of nucleic acids, this results in the trapping of nucleic acids in the gel-based ion exchangers, thereby severely hampering analysis. Thus, the use of gel-based ion exchangers for desalting nucleic acids can give inconsistent results.

A need exists for a method of desalting samples comprising nucleic acids that overcomes the limitations and problems of the current methods and further allows for efficient high-throughput analysis while avoiding time-consuming and laborious conventional desalting steps.

SUMMARY OF THE INVENTION

The present invention is drawn to methods of desalting a sample comprising a nucleic acid.

In the methods of the invention, a liquid sample containing a nucleic acid and a salt is contacted with an ion exchanger that comprises an insoluble phosphate salt, under conditions for binding of the nucleic acid to the ion exchanger. The liquid sample is then removed and the nucleic acid is subsequently eluted from the ion exchanger. The ion exchangers used in the invention comprise an insoluble phosphate salt which can be, for example, zirconium phosphate, hafnium phosphate or titanium phosphate, or any combination thereof. In one embodiment, the salt to be desalted from a nucleic acid comprises sodium ($Na^+$) cations or potassium ($K^+$) cations.

The methods of the invention can be used to desalt samples comprising a variety of nucleic acids, including, for example, single-stranded nucleic acids and double-stranded nucleic acids. Such nucleic acids include deoxyribonucleic acids (DNA)(e.g., genomic DNA, cDNA, chromosomal DNA, plasmid DNA), ribonucleic acids (RNA)(e.g., messenger RNA (mRNA), transfer RNA (tRNA), ribosomal RNA (rRNA)), deoxyribonucleic acid-ribonucleic acid hybrids (DNA-RNA hybrids) and nucleic acids comprising deoxyribonucleotides and/or ribonucleotides. The methods of the invention are applicable not only to nucleic acids which are comparatively large in size (e.g., chromosomal DNA, genomic DNA) but also to those which are comparatively small in size (e.g., oligonucleotides). In one embodiment, the methods of the invention are used to desalt single-stranded and/or double-stranded oligonucleotides.

The methods of the invention can be used for naturally-occurring nucleic acids, for example, naturally-occurring nucleic acids which are isolated from an organism, including mammals and in particular, humans. Alternatively, the methods of the invention can be used for modified nucleic acids, such as, for example, a nucleic acid which was isolated from an organism, and then modified to alter (e.g., add, delete, or change) one or more nucleotides; the methods can also be used for recombinantly-produced nucleic acids. The methods of the invention can also be used for synthetic nucleic acids; that is, nucleic acids which are prepared by artificial means, rather than isolated from an organism. For example, the synthetic nucleic acid can be produced using an automated synthesizer. Examples of synthetic or modified nucleic acids include nucleic acids which contain nucleotides or nucleic acid analogs that are normally not found in nature, for example, phosphorothioates, protein-nucleic acids, protein-nucleic acid hybrids and synthetic nucleic acids comprising at least one modified nucleotide (e.g., a dideoxynucleotide, a biotinylated nucleotide, an amine-modified nucleotide, an alkylated nucleotide, a fluorophore-labeled nucleotide, a radiolabeled nucleotide). Nucleic acids (both naturally-occurring and synthetic) can be isolated or produced using a variety of means, for example, wherein the nucleic acid is a polymerase chain reaction product or a minisequencing product. In one embodiment, the methods can be used for liquid samples containing more than one type of nucleic acid (e.g., a liquid sample containing a naturally-occurring nucleic acid and a modified nucleic acid).

In the methods of the invention, a liquid sample comprising a nucleic acid and a salt is contacted with an ion exchanger under conditions for binding of the nucleic acid to the ion exchanger. In one embodiment, the conditions for binding of the nucleic acid to the ion exchanger comprise an acidic pH (e.g., a pH less than 6). The methods of the invention can also be used for a wide range of sample volumes, including small volumes (e.g., volumes between 10 and 40 µL).

Subsequently, the nucleic acid is eluted from the ion exchanger. In one embodiment, the nucleic acid is eluted from the ion exchanger using a solution which comprises an alkaline pH (e.g., a pH greater than 8). In another embodiment, one or more washing steps is performed while the nucleic acid is bound to the ion exchanger (i.e., prior to eluting the nucleic acid). Such a washing step can be performed using, for example, an acid (e.g., dilute HCl).

The methods of the present invention avoid the more laborious and time-consuming conventional desalting step(s) which are typically required to desalt nucleic acid samples. The properties of the ion exchangers used in the methods of the present invention allow for rapid and efficient desalting of nucleic acid samples and are amenable to high-throughput assays.

DETAILED DESCRIPTION OF THE INVENTION

Figure 1:
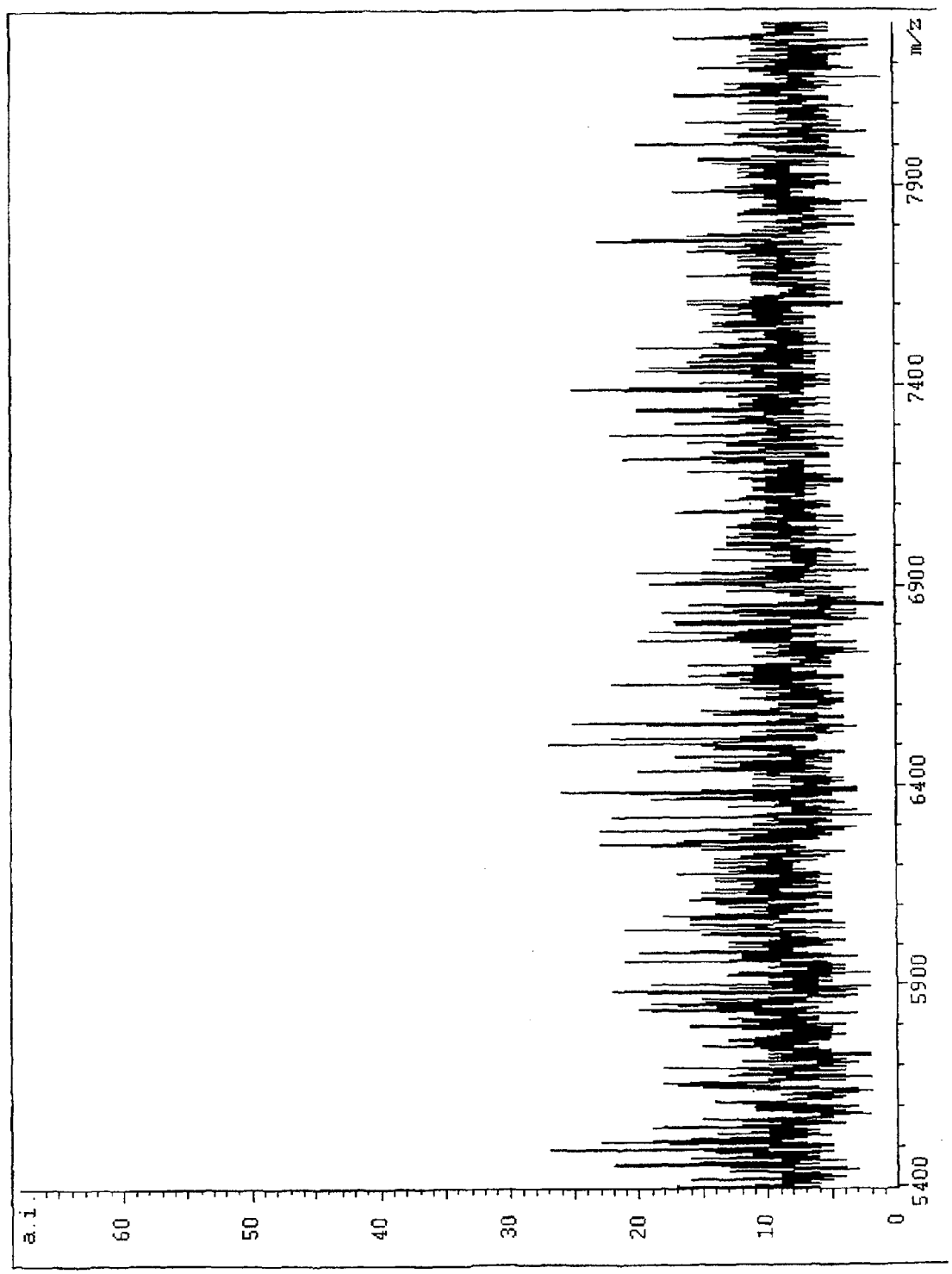
FIG. 1 is a mass spectrum of a 50 mM Na solution containing two oligonucleotides (a 23 'mer T3 Primer at 1.5 µM: 5' TAATACGACTCACTATAGGGAGA 3' (SEQ ID NO:1); and a 20 'mer T7 Primer at 1.5 µM: 5' ATTAACCCTCACTAAAGGGA 3' (SEQ ID NO:2)).

A description of preferred embodiments of the invention follows.

As described herein, the present invention is drawn to methods of desalting samples comprising a nucleic acid. As used herein, the term "desalting" refers to separating or removing an ionic salt from a nucleic acid and/or from a sample containing a nucleic acid.

A nucleic acid, as defined herein, comprises an oligomer or polymer of nucleotides which are covalently linked by phosphodiester bonds. Nucleotides have a common structure comprising a phosphate group which is linked by a phosphoester bond to a pentose which in turn is linked to an organic base. If the pentose is ribose, the nucleic acid is RNA and the nucleotides are ribonucleotides. If the pentose is 2-deoxyribose, the nucleic acid is DNA and the nucleotides are deoxyribonucleotides. In aqueous solutions which have a pH greater than about 2, the very hydrophilic sugar-phosphate polymer backbone of a nucleic acid contributes one negative charge for each phosphodiester plus one or two negative charges for every terminal phosphomonoester. Thus, nucleic acids are polyanions which possess a net negative charge which is approximately proportional to the length of the nucleic acid. Any of a wide variety of bases may be attached to the pentose, but the five that predominate in naturally-occurring DNA and RNA are adenine ("A"), thymine ("T", primarily in DNA), uracil ("U", primarily in RNA), guanine ("G"), and cytosine ("C").

As used herein, the term "nucleotide" encompasses not only nucleotides (ribonucleotides and deoxyribonucleotides), but also encompasses related molecules including nucleosides (nucleotides lacking a 5'-phosphate) and phosphodiesters (nucleotides lacking a nitrogen-containing heterocyclic organic base). Furthermore, as used herein, the terms "oligonucleotide" and "polynucleotide" are interchangeable and refer to a nucleotide multimer or oligomer which is composed of deoxyribonucleotides or ribonucleotides, or a combination thereof, having from a few, e.g., 2–20, to many, e.g., 20 to several hundred or more, nucleotides. The terms also encompass chains of nucleosides which are linked by analogs of the phosphate linkages, e.g., phosphorothioate, phosphoramidate, alkylphosphonate, alkylphosphonothioate, and the like, or combinations thereof. The nucleic acids can include double-stranded and/or single-stranded nucleic acids; they can be single-stranded or double-stranded DNA, RNA or DNA-RNA hybrids.

Nucleic acids can include naturally-occurring nucleic acids; "naturally-occurring" nucleic acids, as used herein, are nucleic acids that are found in an organism, for example, genomic DNA, complementary DNA (cDNA), chromosomal DNA, plasmid DNA, mRNA, tRNA, and/or rRNA. In another embodiment of the invention, the nucleic acids can comprise modified nucleic acids. "Modified" nucleic acids include, for example, nucleic acids which are naturally-occurring, as described above, but are modified to alter (e.g., add, delete, or modify) one or more nucleotides. In another embodiment, the nucleic acids can include synthetic nucleic acids, including but not limited to, nucleic acids prepared on solid phases using well-known and/or commercially-available procedures, e.g., using an automated nucleic acid synthesizer. In yet another embodiment, a combination of more than one type of nucleic acids can be present (e.g., naturally-occurring and/or modified and/or synthetic nucleic acids).

The naturally-occurring, modified and/or synthetic nucleic acids can comprise modified nucleotides. As used herein, a modified nucleotide is a nucleotide that has been structurally altered so that it differs from a naturally-occurring nucleotide. Such modified nucleotides include nucleotides which contains a modified sugar moiety, a modified phosphate moiety and/or a modified nucleobase.

Modification of the sugar moiety includes, but is not limited to, replacement of the ribose ring with a hexose, cyclopentyl or cyclohexyl ring. Alternatively, the D-ribose ring of a naturally-occurring nucleic acid can be replaced with an L-ribose ring or the β-anomer of a naturally-occurring nucleic acid can be replaced with the α-anomer.

Modified phosphate moieties include phosphorothioates, phosphorodithioates, methyl phosphonates, alkylphosphonates, alkylphosphonothioates, methyl phosphates, phosphoramidates, and the like, or combinations thereof. Nucleic acids which comprise such modified phosphate linkages can have improved properties when compared to a corresponding nucleic acid which comprises only phosphate diester linkages. For example, nucleic acids comprising modified linkages can have increased resistance to degradation by nucleases which may be present in an organism (e.g., when used in antisense applications).

Modified nucleobases include 7-deazaguanine, 7-deaza-8-azaguanine, 5-propynylcytosine, 5-propynyluricil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouricil, 2,6-diaminopurine, 8-aminopurine, 4-triazolo-5-methylthymine, and 4-triazolo-5-methyluricil. Modified nucleobases can also include abasic moieties. Methods for generating nucleic acids which comprise one or more modified sugar moieties, phosphate moieties and/or nucleobases are well known to those of skill in the art.

Modified nucleotides also encompass conjugated nucleotides (e.g., nucleotides conjugated to a moiety). Examples of such modified nucleotides include but are not limited to, dideoxynucleotides, biotinylated nucleotides, amine-modified nucleotides, alkylated nucleotides, fluorophore-labeled nucleotides, radiolabeled nucleotides, phosphorothioates, phosphoramidites, phosphites, ring atom-modified derivatives and the like. Nucleic acids can further encompass nucleic acid polymers which possess a modified backbone, such as protein-nucleic acids (PNAs) or PNA hybrids. Methods for producing modified nucleotides and/or nucleic acid polymers which possess a modified backbone, e.g., PNA, PNA hybrid, are well known to those of skill in the art.

A modified nucleotide can be produced by a chemical modification of a nucleotide, either prior to, during, or subsequent to incorporation into a nucleic acid, for example, using methods that are well known in the art. Alternatively, a modified nucleotide can be produced by incorporating a modified nucleoside triphosphate into a nucleic acid polymer chain during an amplification reaction, for example, a polymerase chain reaction (PCR), a minisequencing reaction. Nucleic acids containing multiple modified nucleotides and/or any combination of modified nucleotides are also encompassed by the invention. Also included in the invention are chimeric oligonucleotides, for example, an oligonucleotide that contains both phosphodiester and phosphorothioate linkages.

Nucleic acids subjected to the methods of the invention can be obtained from various biological and/or chemical materials using procedures that are well known to those of skill in the art. Naturally-occurring nucleic acids can be obtained from organisms, tissues, and/or cells from veterinary or human clinical test samples collected for diagnostic and/or prognostic purposes, for example, diagnosis or prognosis of a particular disease or disorder. For example, cells can be lysed and the resulting lysate can be processed using techniques familiar to one of skill in the art to obtain an aqueous solution of nucleic acid (e.g., DNA and/or RNA) (see, for example, Ausebel, F., et al., *Current Protocols in Molecular Biology*, Wiley, New York (1988); Maniatis, et al., *Molecular Cloning: A Laboratory Manual*, Cold Spring Harbor Laboratory, Cold Spring Harbor, N.Y. (1982)). Nucleic acids, where appropriate can also be cleaved to obtain a fragment that contains a desired nucleotide sequence, for example, by treatment with a restriction endonuclease or other site-specific chemical cleavage methods. Nucleic acids can also be synthesized from nucleotide monomers, e.g., using an automated nucleic acid synthesizer, or can be obtained using recombinant DNA methodology. In a preferred embodiment, the invention is a method of desalting a liquid sample comprising a mammalian nucleic acid (e.g., a human nucleic acid).

In the methods of the invention, the nucleic acid can be present in a liquid sample. Liquid samples comprising nucleic acids include samples which comprise naturally-occurring nucleic acids, including but not limited to, nucleic acids isolated from living or dead naturally-occurring or artificially-grown unicellular or multicellular organisms, including eukaryotic (e.g., animals, plants) and prokaryotic organisms (e.g., bacteria). Liquid samples comprising nucleic acids also include eukaryotic or prokaryotic cells in culture; cells taken or obtained from tissues or bodily fluids from an animal (e.g., a mammal, such as a human), including but not limited to, blood, lymphatic fluid, cerebral spinal fluid, urine, feces, synovial fluid, bile, phlegm, saliva, aqueous humor, lacrimal fluid, menstrual fluid and semen; embryos or fetuses; food stuffs; cosmetics; or any other source of cells. Liquid samples comprising nucleic acids include plant fluids, for example, xylem fluid, phloem fluid, plant exudates, as well as samples comprising organelles (e.g., mitochondria, chloroplasts), viruses, phages, plasmids, viroids, parasites, molds, fungi, or the like that infect cells.

Nucleic acids used in the methods of the invention can also be subjected to various molecular biological and/or separation techniques, prior to and/or subsequent to, being utilized in the methods of the invention. For example, nucleic acids can be subjected to separation techniques including but not limited to, affinity separation (e.g., nucleic acid hybridization), electrophoretic separation (e.g., using size-fractionation agarose or polyacrylamide gels) and/or chromatographic separation (e.g., ion exchange chromatography, high pressure liquid chromatography (HPLC)). In cases where nucleic acids are subjected to gel electrophoresis prior to being utilized in the methods of the invention, the nucleic acids will typically be separated from the gel matrix, for example, by eluting the DNA from a slice of the gel into a solution, melting the slice of gel, or otherwise degrading the gel slice in a solution (see, for example, Ausebel, F., et al., *Current Protocols in Molecular Biology*, Wiley, New York (1988); Maniatis, et al., *Molecular Cloning: A Laboratory Manual*, Cold Spring Harbor Laboratory, Cold Spring Harbor, N.Y. (1982)). Nucleic acids can also be modified, as described above.

If desired, the nucleic acids can be subjected to some form of amplification process, for example, the polymerase chain reaction (PCR) or a minisequencing reaction. Appropriate techniques for amplifying particular nucleic acids are well known to those of skill in the art and are encompassed by the present invention. In one embodiment, a liquid sample comprising a nucleic acid which is a product of an amplification process, for example, a PCR product or a minisequencing product, is subjected to the methods of the invention.

The nucleic acids desalted by the methods of the invention can be present in a wide variety of liquid samples. Representative liquid samples include any solution or suspension which comprises a nucleic acid, including samples containing naturally-occurring oligonucleotides (e.g., samples containing nucleic acids found in a living or dead naturally-occurring or artificially-grown unicellular or multicellular organism), synthetic oligonucleotides (e.g., a sample obtained from an automated nucleic acid synthesizer) or recombinantly-produced nucleic acids. Other representative liquid samples include but are not limited to, water and buffered solutions (e.g., Tris-based solutions, MOPS-based solutions, HEPES-based solutions, acetate-based solutions, phosphate-based solutions, and the like). Also included are solutions typically used in chemical and/or biological applications, for example, solutions containing reagents used in the synthesis of a nucleic acid (e.g., solutions containing PCR buffers and reagents, solutions containing minisequencing buffers and reagents, solutions containing reagents for automated synthesis of a nucleic acid), solutions containing reagents used in the sequencing of a nucleic acid and solutions used in the separation of a nucleic acid (e.g., solutions used in chromatographic separation). Other liquid samples and/or solutions which are suitable for the methods of the invention are well known to those of skill in the art. Liquid samples which contain a combination of more than one type of nucleic acid (e.g., a sample comprising both naturally-occurring and synthetic nucleic acids) are also encompassed by the invention.

The methods of the present invention can be performed on a wide range of volume of liquid samples, including very small volumes (e.g., 40 $\mu$L or less). In one embodiment, the invention is performed on a liquid sample having a volume between about 10 $\mu$L and about 40 $\mu$L. Thus, the methods of the invention can be used to desalt nucleic acids which are amplification products (e.g., PCR products, minisequencing products), since many of these reactions are performed in small volumes (e.g., 40 $\mu$L or less). The methods of the invention can also be performed on volumes of liquid sample which are less than 10 $\mu$L as long as the liquid sample can be clearly separated from the ion exchanger. In other embodiments, the methods of the invention can be performed on liquid samples having volumes between about 10 $\mu$L and about 50 $\mu$L, about 10 $\mu$L and about 100 $\mu$L, about 10 $\mu$L and about 250 $\mu$L, or about 10 $\mu$L and about 500 $\mu$L. Much larger volumes of liquid sample (e.g., 500 $\mu$L or more) can also be used in the methods of the invention, using enough ion exchanger to bind the nucleic acid present in the sample.

In the methods of the invention, a liquid sample comprising a nucleic acid is contacted with an ion exchanger comprising an insoluble salt, under conditions for binding of the nucleic acid to the ion exchanger. Binding of the nucleic acid to the ion exchanger may be mediated by hydrogen binding between the surface phosphate of the ion exchanger and the backbone phosphate of the nucleic acid. In low pH solutions, the phosphates of the ion exchanger and/or nucleic acid are protonated which can allow for hydrogen bonding to occur between the nucleic acid and the ion exchanger. At higher pH, the phosphates of the ion exchanger and/or nucleic acid become deprotonated which can disrupt hydrogen binding and thereby release the nucleic acid from the ion exchanger.

In one embodiment, the conditions for binding of a nucleic acid to an ion exchanger comprise an acidic pH. As defined herein, an acidic pH is a pH less than 7. In another embodiment, the conditions for binding of a nucleic acid to an ion exchanger comprise a pH less than 6. In another embodiment, elution of the nucleic acid from the ion exchanger is performed using a solution which comprises an alkaline pH. As defined herein, an alkaline pH is a pH greater than 7. In another embodiment, elution of the nucleic acid from the ion exchanger is performed using a solution which comprises a pH greater than 8.

In the methods of the invention, a sample comprising the nucleic acid also comprises one or more salts. As defined herein, a salt is an ionic compound (i.e., a compound containing positive and negative ions). Preferably, the salt in the sample is a water-soluble inorganic salt. Because of its polarity, water interacts with ionic and/or polar substances. Typically, the numerous polar water molecules compete with the relatively few positively- and negatively-charged ions of the salt, thereby causing the salt to dissociate. Each positive ion of the salt (cation) attracts the negative ends of several water molecules while each negative ion (anion) of the salt attracts the positive ends of several water molecules. These hydrated ions, and in particular the positively-charged hydrated cations, can then interact with the negatively-charged sugar phosphate backbone of a nucleic acid.

In the methods of the invention, a sample (e.g., a liquid sample) comprising a nucleic acid and a salt is contacted with an ion exchanger, under conditions for binding of the nucleic acid to the ion exchanger. The liquid sample is then removed and the nucleic acid is eluted from the ion exchanger. The actual separation of the salt from the sample containing the nucleic acid can occur by a variety of mechanisms. For example, if the salt is water-soluble and fails to bind to the nucleic acid or the ion exchanger (or binds with very low affinity), it can be removed when the liquid sample is removed (i.e., after binding of the nucleic acid to the ion exchanger but before the nucleic acid is eluted). Alternatively, if the water-soluble salt binds to the nucleic acid and/or the ion exchanger with an affinity that is less than the affinity of the binding of the nucleic acid to the ion exchanger, it can be removed by washing the ion exchanger with nucleic acid bound thereon, with a suitable washing solution (i.e., prior to eluting the nucleic acid from the ion exchanger). Finally, if the water-soluble salt binds to the ion exchanger with an affinity that is greater than the affinity of the binding of the nucleic acid to the ion exchanger, it can remain bound to the ion exchanger and may not be eluted with the nucleic acid, when an appropriate eluting solution is used. In a preferred embodiment, the salt fails to bind to the nucleic acid or the ion exchanger (or binds with very low affinity relative to the binding of the nucleic acid to the ion exchanger) and can be removed when the liquid sample is removed.

As described above, the ion exchanger with nucleic acid bound thereon, can be subjected to one or more washing steps prior to elution. Thus, in one embodiment, the method of the invention comprises washing of the ion exchanger with nucleic acid bound thereon (e.g., using one or more washing steps), prior to elution of the nucleic acid from the ion exchanger. In addition to removing salt from the ion exchanger-nucleic acid complex, the one or more washing steps can also remove other contaminants present in the sample which associate with the ion exchanger and/or nucleic acid. Appropriate solutions for washing the ion exchanger with nucleic acid bound thereon are those that do not disrupt the interaction between the nucleic acid and the ion exchanger, e.g., washing solutions that have an appropriate pH and can remove salt and contaminants without causing the nucleic acid to release from the ion exchanger. Such washing solutions include but are not limited to, acidic solutions (e.g., dilute HCl(e.g., 0.1 M HCl)) and acidic-buffered solutions (e.g., Tris-based solutions, MOPS-based solutions, HEPES-based solutions, acetate-based solutions, phosphate-based solutions). In one embodiment, the washing solution is an acid (e.g., dilute HCl (e.g., 0.1 M HCl)) which is at a sufficiently dilute enough concentration such that it does not degrade the nucleic acid. In another embodiment, the washing solution comprises an acidic-buffered solution which does not contain the cation(s) which are being desalted. For example, where it is desired to remove sodium ($Na^+$) and/or potassium ($K^+$) cation(s), a washing solution that does not comprise these cation(s) is used.

As described above, in the methods of the invention, the nucleic acid is eluted from the ion exchanger (after removal of the liquid sample). Appropriate eluting solutions are those that cause release of the nucleic acid from the ion exchanger. Such eluting solutions include solutions which comprise an alkaline pH (e.g., solutions with a pH greater than 7). For example, eluting solutions include but are not limited to solutions buffered to achieve an alkaline pH (e.g., Tris-based solutions, MOPS-based solutions, HEPES-based solutions, acetate-based solutions, phosphate-based solutions), solutions which contain one or more ionic salts (e.g., NaCl, KCl, $MgCl_2$, $CaCl_2$, $NaHCO_3$, $Na_2CO_3$, NaOH, $NH_4OH$, and the like) and other solutions used to elute nucleic acids which are known in the art. In one embodiment, the alkaline-buffered eluting solution does not comprise the cation(s) which were desalted. For example, in situations where it is desired to remove sodium ($Na^+$) and/or potassium ($K^+$) cation(s), the eluting solution should not contain these cation(s). In another embodiment, the eluting solution is a solution which comprises $NH_4OH$ (e.g., 0.1 M $NH_4OH$).

The methods of the invention remove inorganic water-soluble ionic salts, and in particular the cations of an ionic salt, from a sample containing a nucleic acid and/or from a nucleic acid. Two important cations which are commonly associated with nucleic acids and typically require removal are sodium ($Na^+$) and potassium ($K^+$). Thus, in one embodiment, the salt removed from the sample comprises sodium and/or potassium. Inorganic water-soluble ionic salts which can be removed by the methods of the invention include, but are not limited to, salts containing the cations listed in Table 1 and/or anions listed in Table 2.

TABLE 1

| Cations | |
|---|---|
| Name | Formula |
| Aluminum | $Al^{3+}$ |
| Ammonium | $NH_4^+$ |
| Barium | $Ba^{2+}$ |
| Cadmium | $Cd^{2+}$ |
| Calcium | $Ca^{2+}$ |
| Chromium(III) | $Cr^{3+}$ |
| Cobalt(II) | $Co^{2+}$ |
| Copper(II) | $Cu^{2+}$ |
| Copper(I) | $Cu^+$ |
| Iron(III) | $Fe^{3+}$ |
| Iron(II) | $Fe^{2+}$ |
| Lead | $Pb^{2+}$ |
| Lithium | $Li^+$ |
| Magnesium | $Mg^{2+}$ |
| Manganese | $Mn^{2+}$ |
| Mercury(II) | $Hg^{2+}$ |
| Mercury(I) | $Hg_2^{2+}$ |
| Nickel | $Ni^{2+}$ |
| Potassium | $K^+$ |
| Silver | $Ag^+$ |
| Sodium | $Na^+$ |
| Tin(II) | $Sn^{2+}$ |
| Zinc | $Zn^{2+}$ |

TABLE 2

| Anions | |
|---|---|
| Name | Formula |
| Acetate | $CH_3COO^-$ |
| Bromide | $Br^-$ |
| Carbonate | $CO_3^{2-}$ |
| Chlorate | $ClO_3^-$ |
| Chloride | $Cl^-$ |
| Chlorite | $ClO_2^-$ |
| Chromate | $CrO_4^{2-}$ |
| Cyanate | $CNO^-$ |
| Cyanide | $CN^-$ |
| Dichromate | $Cr_2O_7^{2-}$ |
| Dihydrogen phosphate | $H_2PO_4^-$ |

TABLE 2-continued

| Anions | |
|---|---|
| Name | Formula |
| Fluoride | $F^-$ |
| Hydrogen carbonate | $HCO_3^-$ |
| Hydrogen phosphate | $HPO_4^{2-}$ |
| Hydrogen sulfate | $HSO_4^-$ |
| Hydrogen sulfite | $HSO_3^-$ |
| Hypochorite | $ClO^-$ |
| Hydride | $H^-$ |
| Iodide | $I^-$ |
| Nitrate | $NO_3^-$ |
| Nitrite | $NO_2^-$ |
| Oxalate | $C_2O_4^{2-}$ |
| Oxide | $O^{2-}$ |
| Perchlorate | $ClO_4^-$ |
| Permanganate | $MnO_4^-$ |
| Peroxide | $O_2^{2-}$ |
| Phosphate | $PO_4^{3-}$ |
| Silicate | $SiO_4^{4-}$ |
| Sulfate | $SO_4^{2-}$ |
| Sulfide | $S^{2-}$ |
| Sulfite | $SO_3^{2-}$ |
| Superoxide | $O_2^-$ |
| Thiocyanate | $SCN^-$ |
| Thiosulfate | $S_2O_3^{2-}$ |

The methods of the invention utilize ion exchangers to desalt nucleic acids. As described herein, an ion exchanger is a composition which contains fixed negative or positive charges that are capable of binding molecules of opposite charge. In one embodiment, the ion exchanger is a solid. In the neutral state, ion exchangers contain displaceable ions of opposite charge (counterions). If the ion exchanger contains negative charge, the displaceable ions (counterions) will be positively charged and the material is known as a cation exchanger. If the ion exchanger contains positive charge, the displaceable ions (counterions) will be negatively charged and the material is known as an anion exchanger. In one embodiment of the invention, the ion exchanger is a cation exchanger.

The ion exchangers can contain inorganic materials or organic materials. Examples of organic materials include but are not limited to, clays, zeolites and resinous organic materials. Examples of inorganic ion exchangers include but are not limited to, phosphates, antimonates, oxide-containing compounds, hydroxides, vanadates, cyanates, silicates and acids. Representative inorganic materials which possess varied selectivity for cations include zirconium phosphate, hafnium phosphate and titanium phosphate. Other inorganic ion exchangers possessing selectivity for cations include antimony trioxide, antimony pentoxide, hydrous antimony oxide (V), titanium antimonate, zirconium antimonate, tin antimonate, iron antimonate, aluminum antimonate, chromium antimonate, tantalum antimonate, manganese antimonate, bismuth antimonate, phosphoantimonic acid, antimonotungstic acid, ammonium antimonomolybdate, bismuth phosphate, tin phosphate, vanadium pentoxide, hydrous vanadium pentoxide, titanium vanadate, aluminum vanadate, zirconium vanadate, phosphovanadic acid, vanadinomolybdenic acid, vanadium ferrocyanate, niobium pentoxide, hydrous niobium pentoxide, tantalum pentoxide, hydrous tantalum pentoxide, tantalum phosphate, ferrous hydroxide, aluminum hydroxide, manganese oxide, thorium phosphate, cerium phosphate and aluminum phosphate. Preferably, the ion exchangers used in the methods of the invention are inorganic solid compositions.

In a preferred embodiment, the inorganic ion exchanger comprises an insoluble phosphate salt. As used herein, an insoluble phosphate salt is a phosphate salt which is substantially insoluble in water and in solvents normally used for ion exchange separations. Examples of insoluble phosphate salts include but are not limited to, zirconium phosphate, hafnium phosphate, titanium phosphate, bismuth phosphate, tin phosphate, tantalum phosphate, thorium phosphate, cerium phosphate and aluminum phosphate. Preferably, the inorganic ion exchangers used in the methods of the invention comprise one or more insoluble phosphate salts which have a higher binding affinity for the negatively-charged sugar phosphate backbone of a nucleic acid than the ionic salt desired to be removed.

In particular embodiments, the ion exchangers used in the methods of the invention comprise an insoluble phosphate salt which is selected from the group consisting of zirconium phosphate, hafnium phosphate and titanium phosphate. In a preferred embodiment, the insoluble phosphate salt is zirconium phosphate. Ion exchangers used in the methods of the invention also include combinations of two or more of any of the above-listed compounds. Moreover, additional ion exchangers (e.g., insoluble ion exchangers and/or ion exchangers which are known in the art and are suitable for desalting nucleic acids) can be utilized in conjunction with the ion exchangers of the invention.

Ion exchangers which comprise an insoluble phosphate salt in any form or structure are encompassed by the present invention. For example, it has been reported that zirconium phosphate can exist in at least 10 different crystalline phase. Moreover, zirconium phosphate typically exists as a hydrate having from between about 0.1 moles of water at 700° C. to about 2 moles of water at 120° C. (see, for example, U.S. Pat. No. 4,521,528). For the methods of the invention, the precise structure of the insoluble phosphate salt, e.g., zirconium phosphate, hafnium phosphate, titanium phosphate, is not a limitation and all forms of such insoluble phosphate salts are encompassed by the invention.

The insoluble phosphate salts used in the methods of the invention, e.g., zirconium phosphate, hafnium phosphate, titanium phosphate, can be prepared by methods known in the art. For example, methods of producing zirconium phosphates are disclosed in U.S. Pat. Nos. 3,056,647, 3,485,763, 4,025,608, 4,381,289 and 4,521,528 and in Clearfield and Stynes (Clearfield, A. and Stynes, J. A., *J. Inorg. Nucl. Chem.* 26:117 (1964)) and Alberti and Torraca (Alberti, G and Torraca, E., *J. Inorg. Nucl. Chem.* 30:317 (1968)). Methods of producing hafnium phosphates are disclosed in U.S. Pat. No. 4,521,528.

The concentration and amount of ion exchanger used in the methods of the present invention can be adjusted for the quantity and nature of the liquid sample being subjected to the method, and the concentration and nature of the nucleic acid(s) and ionic salt(s) in the sample. One of ordinary skill in the art can easily determine an appropriate amount of ion exchanger for desalting nucleic acids in a particular sample without having to perform undue experimentation. For example, a person of ordinary skill in the art could vary the concentration of the ion exchanger (e.g., cation exchanger) and could measure the ionic strength of the ion (e.g., cation) using an ion-specific electrode (e.g., a cationic-specific electrode) if one is available. Alternatively, one could set up conditions such that the cation to be desalted is in an equimolar ratio to the base in the alkaline solution, and the cation exchanger is its hydrated form (and thereby releases cations (e.g., $H^+$ ions) when exchange occurs). One could then measure the pH of the solution at different concentrations of cation exchanger to determine the extent of cationic exchange. Other suitable methods for determining an appropriate concentration of ion exchanger, e.g., those known in the art, could also be used.

Similarly, the time for contact of the nucleic acid in a liquid sample with an ion exchanger can be adjusted for the quantity and nature of the sample, the concentration and type of ionic salt(s) in the sample and the ratio of the ion exchanger to ionic salt(s). The appropriate time required for contact of the ionic salt(s) in the liquid sample with the ion exchanger can easily be determined by one of ordinary skill in the art without having to perform undue experimentation, e.g., using the methods described above. In one embodiment, binding of a suitable concentration of ion exchanger and nucleic acid occurs on the order of seconds (e.g., within 5 seconds).

Prolonged exposure of the eluted nucleic acid with the ion exchanger (e.g., greater than 15 minutes) should be avoided as it can result in the loss of product due to the solution becoming acidic. Thus, after elution of the nucleic acid from the ion exchanger, eluted nucleic acid can be separated from the ion exchanger. Generally, the ion exchanger comprising the insoluble phosphate salt will settle to the bottom of a sample container. Alternatively, a brief centrifugation spin (e.g., less than a minute) will cause the ion exchanger to settle to the bottom of the sample container and the liquid, containing the eluted nucleic acid, can easily be removed by standard methods, e.g., by pipetting, filtering or other method known in the art.

The nucleic acids desalted by the methods of the invention can be subjected to analysis using a wide variety of methods, including, for example, mass spectrometry, particularly MALDI-TOF MS. MALDI-TOF MS is particularly well suited for high-throughput analysis and has been applied to many different areas of nucleic acid analysis, including but not limited to, mutation and polymorphism analysis (for example, single-nucleotide polymorphism (SNP) analysis) (Griffin, T. J. and Smith, L. M., *Trends Biotechnol.* 18:77–84 (2000), Jurinke, C. et al., *Anal. Biochem.* 237:174–181 (1996); Higgins G. S. et al., *Biotechniques* 23:710–714 (1997)), sequencing (Fu, D-J et al., *Nat. Biotechnol.* 16:381–384 (1996); Köster H. et al., *Nature Biotechnology* 14:1123–1128 (1996)) and virus and/or bacterial detection (Jurinke, C. et al., *Genetic Analysis: Biomolecular Engineering* 13:67–71 (1996); Hurst G. B. et al., *Rapid Commun. Mass Spectrom.* 10:377–382 (1996)). The use of MALDI-TOF MS for SNP analysis has been successfully applied to the genotyping of SNPs located in a number of biologically-important genes (see, for example, Braun et al., *Genomics* 46:18–23 (1997); Little et al., *Eur. J. Clin. Chem. Clin. Biochem.* 35:545–548 (1997); Little et al., *Nat. Med.* 3:1413–1416 (1997)).

Analyzing nucleic acids with MALDI-TOF MS has several advantages over other nucleic acid analytic methods. First, MALDI-TOF MS is incredibly rapid. Ionization, separation by size and detection of nucleic acids takes milliseconds to complete and acquisition and analysis of multiple laser pulses (typically 20–100 pulses) can take less than a minute. In contrast, conventional electrophoretic methods for separating and detecting nucleic acids can take hours to complete. Second, MALDI-TOF MS produces data of absolute mass value, an intrinsic property of a molecule. This is inherently more accurate than relative-based techniques, such as electrophoretic- or hybridization-based techniques, which are susceptible to complications which arise from secondary structure formation in nucleic acids (e.g., secondary structure arising from GC-rich sequences). Third, automation of all of the steps of MALDI-TOF MS, ranging from sample preparation through to acquisition and processing of data, is feasible. As such, MALDI-TOF MS is an ideal technique for high-throughput analysis of nucleic acids.

The methods of the present invention are advantageous in that they avoid the more laborious and time-consuming conventional desalting step(s) which are typically required to desalt nucleic acid samples. The properties of the ion exchangers used in the methods of the present invention allow for rapid and efficient desalting of nucleic acids. Thus, the methods of the invention are amenable and well suited for use in high-throughput assays. For example, the methods of the invention can be incorporated in high-throughput methods for analyzing nucleic acids (e.g., high-throughput MALDI-TOF MS methods for analyzing nucleic acids).

In addition, the methods of the present invention can be used for nucleic acids present in a wide variety of liquid samples, including, for example, a sample that is a product of an amplification process (e.g., a PCR product, a minisequencing product) without having to first perform any additional separation or purification steps. In cases where nucleic acids are subjected to chromatographic separation prior to being utilized in the methods of the invention, the present invention eliminates one or more separate desalting steps that would otherwise be necessary because chromatographic separation of nucleic acids typically requires that a salt gradient be used to elute the nucleic acids off of the exchange composition (e.g., anion exchange composition) prior to analysis and/or use. Thus, the methods of the invention can be used with both untreated samples (e.g., PCR products and/or minisequencing products containing all of the elements required for their production) and treated samples (e.g., samples containing nucleic acids subjected to chromatographic separation) and can avoid the more laborious and time-consuming desalting, separation or purification step(s) which are typically required to desalt and/or purify nucleic acid samples. Moreover, the methods of the invention are particularly well-suited for high-throughput screening and are amenable to automation.

The methods of the invention can further be applied as part of, or in combination with, other methods. For example, the methods of the invention can be used in conjunction with other nucleic acid analytic methods, for, among other things, diagnosing diseases, identifying pathogens, testing foods, cosmetics, blood, blood products or other products for contamination by pathogens, genotyping (e.g., SNP genotyping), forensic testing, paternity testing and sexing of fetuses or embryos.

The invention will be further described by the following non-limiting examples. The teachings of all publications cited herein are incorporated herein by reference in their entirety.

EXAMPLES

Example 1

General Protocol for Desalting a PCR Product Using Zirconium Phosphate Methods An acidic slurry of zirconium phosphate was made by mixing equal amounts of zirconium phosphate powder (Aldrich Chemical Company, Milwaukee, Wis.; Cat. no. 13772-29-7) and 0.1M HCl. 4–6 µL of zirconium phosphate slurry was added to a minisequencing PCR product (10–15 µL of PCR product) and was mixed thoroughly. The mixture was allowed to settle for 1–5 minutes (or was briefly centrifuged) and the liquid was removed by pipetting and was discarded. 10 µL of 0.01 M HCl was added to the sample and was mixed thoroughly. Again, the mixture was allowed to settle for 1–5 minutes (or was briefly centrifuged) and the liquid was removed by pipetting and was discarded. Additional washing steps using 10 µL of 0.01 M HCl could optionally be performed. To elute the PCR product, 10 µL of 0.1 M $NH_4OH$ was added to the sample and was mixed thoroughly. The mixture was allowed to settle for 1–5 minutes (or was briefly centrifuged) and 8–10 µL of the liquid sample containing the desalted PCR product was removed to a clean vial. Alternatively, an appropriate amount of liquid sample containing the desalted PCR product was spotted directly on a MALDI-TOF MS target. The PCR product was not allowed to contact the zirconium phosphate for long periods of time (e.g., 15 minutes or longer) as this could result in loss of product due to the solution becoming acidic.

Example 2

Analysis of PCR Products Using Zirconium Phosphate and MALDI-TOF MS

Methods

Desalting of a sample containing two oligonucleotides (T3 and T7 primers; each at a concentration of 1 µM) in a 45 mM NaOH solution, was carried out using the method described in Example 1. The first oligonucleotide was a 23 'mer: 5' TAATACGACTCACTATAGGGAGA 3' (SEQ ID NO:1) and the second oligonucleotide was a 20 'mer: 5' ATTAACCCTCACTAAAGGGA 3' (SEQ ID NO:2).

Figure 2:
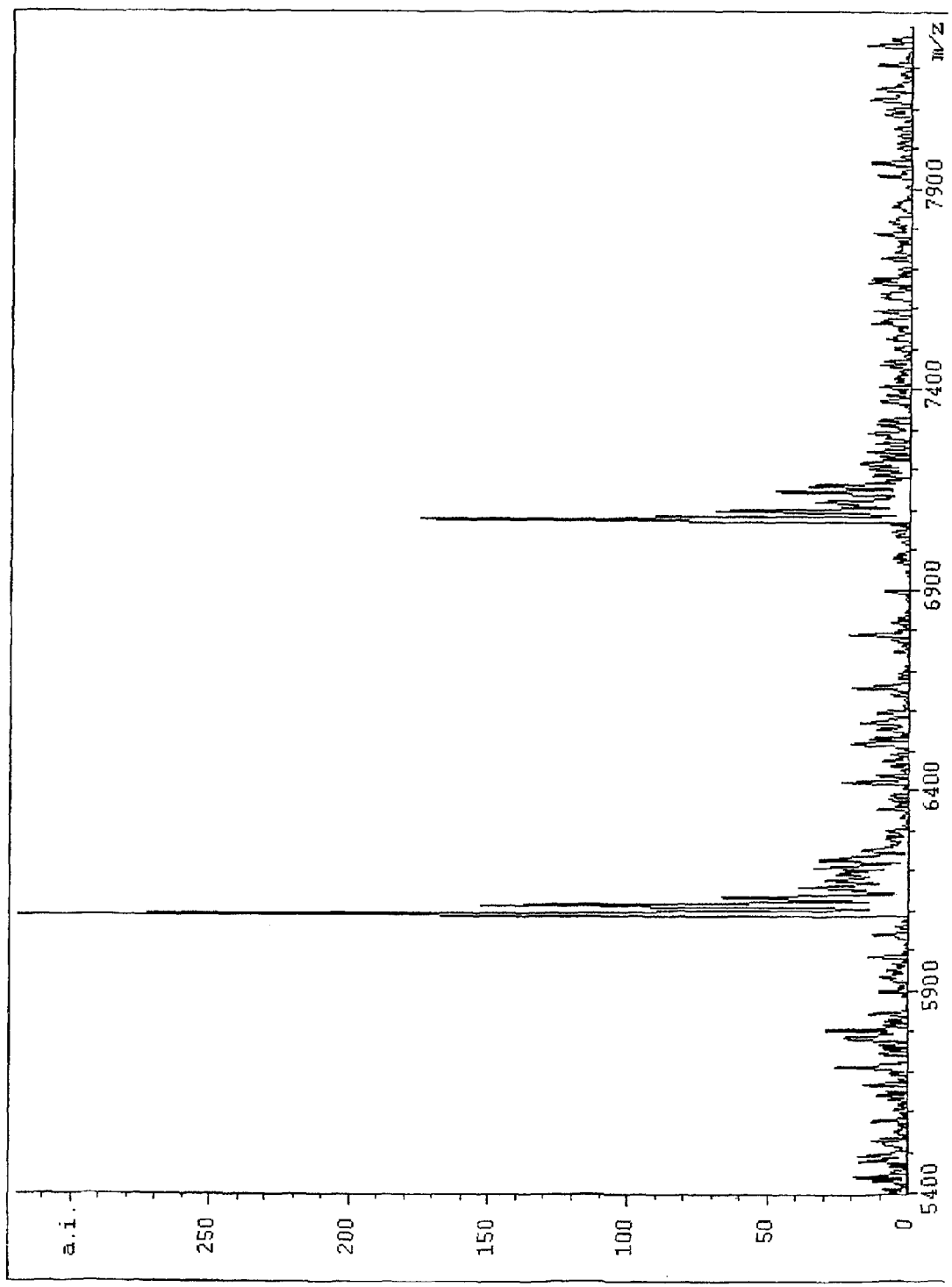
FIG. 2 is a mass spectrum of a 45 mM NaOH solution containing two oligonucleotides (a 23 'mer T3 Primer at 1 µM: 5' TAATACGACTCACTATAGGGAGA 3' (SEQ ID NO:1); and a 20 'mer T7 Primer at 1 µM: 5' ATTAACCCTCACTAAAGGGA 3' (SEQ ID NO:2)) in a 30 µL sample, which has been desalted by adding 4 µL of zirconium phosphate prior to analysis.

The desalted sample was analyzed by MALDI-TOF MS using a Bruker Reflex III MALDI-TOF operated in linear mode, positive polarity (FIG. 2). The operating values were optimized to analyze masses between 3.000 and 10.000 daltons and the matrix which was utilized was a solution of 7 mg/mL 3HPA (3-hydroxypicolinic acid) and 0.7 mg/mL ammonium citrate. The sample (in a ratio of 1:2 sample:matrix) was spotted onto a 400 µm Bruker Anchortarget and was analyzed.

As a control, a 50 mM NaCl solution containing the same T3 and T7 primers (5' TAATACGACTCACTATAGGGAGA 3' (SEQ ID NO:1); and 5' ATTAACCCTGACTAAAGGGA 3' (SEQ ID NO:2)), at a concentration of 1.0 µM, was analyzed using MALDI-TOF MS (FIG. 1).

Results

As depicted in FIG. 2, desalting of a 45 mM Na solution containing two oligonucleotides using zirconium phosphate resulted in two distinct peaks, each peak corresponding to one of the oligonucleotides. In contrast, in the absence of desalting using zirconium phosphate, a 50 mM Na solution containing the same two oligonucleotides produced a mass spectrum that does not reveal the presence of the two oligonucleotides (FIG. 1). Instead, the presence of the salt in the sample results in signal dilution.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for desalting a liquid sample comprising a nucleic acid and a salt, comprising:
   a) contacting said liquid sample under acidic conditions with an ion exchanger, comprising an insoluble phosphate salt selected from the group consisting of:
      zirconium phosphate, hafnium phosphate, titanium phosphate, bismuth phosphate, tin phosphate, tantalum phosphate, thorium phosphate, cerium phosphate aluminum phosphate, and any combination thereof, wherein said nucleic acid to said ion exchanger;
   b) removing said liquid sample; and
   c) eluting said nucleic acid from said ion exchanger using a solution that comprises an alkaline pH.

2. The method of claim 1 wherein said nucleic acid is a naturally-occurring nucleic acid.

3. The method of claim 2 wherein said naturally-occurring nucleic acid is a mammalian nucleic acid.

4. The method of claim 3 wherein said mammalian nucleic acid is a human nucleic acid.

5. The method of claim 1 wherein said nucleic acid is a single-stranded nucleic acid.

6. The method of claim 1 wherein said nucleic acid is a double-stranded nucleic acid.

7. The method of claim 1 wherein said nucleic acid is selected from the group consisting of a deoxyribonucleic acid, a ribonucleic acid and a deoxyribonucleic acid-ribonucleic acid hybrid.

8. The method of claim 7 wherein said nucleic acid is a deoxyribonucleic acid.

9. The method of claim 8 wherein said deoxyribonucleic acid is selected from the group consisting of a genomic DNA, a cDNA, a chromosomal DNA and a plasmid DNA.

10. The method of claim 7 wherein said nucleic acid is a ribonucleic acid.

11. The method of claim 10 wherein said ribonucleic acid is selected from the group consisting of a messenger RNA, a transfer RNA and a ribosomal RNA.

12. The method of claim 1 wherein said nucleic acid is a synthetic nucleic acid.

13. The method of claim 1 wherein said nucleic acid is an oligonucleotide.

14. The method of claim 13 wherein said oligonucleotide is a synthetic oligonucleotide.

15. The method of claim 14 wherein said synthetic oligonucleotide is produced using an automated synthesizer.

16. The method of claim 1 wherein said nucleic acid is a minisequencing product.

17. The method of claim 1 wherein said nucleic acid is a polymerase chain reaction product.

18. The method of claim 1 wherein said nucleic acid comprises deoxyribonucleotides and/or ribonucleotides.

19. The method of claim 12 wherein said nucleic acid comprises at least one modified nucleotide.

20. The method of claim 19 wherein said modified nucleotide is selected from the group consisting of a dideoxynucleotide, a biotinylated nucleotide, an amine-modified nucleotide, an alkylated nucleotide, a fluorophore-labeled nucleotide, a radiolabeled nucleotide, and any combination thereof.

21. The method of claim 1 wherein said liquid sample comprises a sample obtained from a mammal.

22. The method of claim 21 wherein said mammal is a human.

23. The method of claim 1 wherein said acidic conditions comprises a pH less than 6.

24. The method of claim 1 wherein said alkaline pH is a pH greater than 8.

25. The method of claim 1 wherein said liquid sample comprising said nucleic acid has a volume between about 10 $\mu$L and about 40 $\mu$L.

26. The method of claim 1 further comprising analyzing said desalted nucleic acid using matrix-assisted laser desorption-ionization-time-of-flight mass spectrometry.

27. The method of claim 1 further comprising washing said ion exchanger with nucleic acid bound thereon, prior to eluting said nucleic acid from said ion exchanger.

28. The method of claim 27 wherein said washing comprises washing with an acid.

29. The method of claim 28 wherein said acid is HCl.

30. The method of claim 1 wherein said salt comprises sodium cations or potassium cations.

31. The method of claim 1 wherein said nucleic acid comprises from about 2 to about 20 nucleorides.

32. A method for desalting a liquid sample comprising a nucleic acid and a salt, comprising:
 a) contacting said liquid sample under acidic conditions with an ion exchanger comprising an insoluble phosphate salt selected from the group consisting of: zirconium phosphate, hafnium phosphate, titamumn phosphate, and any combination thereof, wherein said nucleic acid binds to said ion exchanger;
 b) removing said liquid sample; and
 c) eluting said nucleic acid from said ion exchanger using a solution that comprises an alkaline pH.

33. A method for desalting a liquid sample comprising a nucleic acid and a salt, comprising:
 a) contacting said liquid sample under acidic conditions with an ion exchanger comprising zirconium phosphate, wherein said nucleic acid binds to said ion exchanger;
 b) removing said liquid sample; and
 c) eluting said nucleic acid from said ion exchanger using a solution that comprises an alkaline pH.

* * * * *

UNITED STATES PATENT AND TRADEMARK OFFICE
CERTIFICATE OF CORRECTION

PATENT NO. : 6,897,027 B2
DATED : May 24, 2005
INVENTOR(S) : Sigurdur V. Smárason and Albert V. Smith It is certified that error appears in the above-identified patent and that said Letters Patent is hereby corrected as shown below:

Column 15,
Line 38, after "acid", add -- binds --.

Signed and Sealed this

Thirtieth Day of August, 2005

JON W. DUDAS
*Director of the United States Patent and Trademark Office*